US00PP28637P2

(12) United States Plant Patent
Sakuramoto

(10) Patent No.: US PP28,637 P2
(45) Date of Patent: Nov. 14, 2017

(54) CARNATION PLANT NAME 'HILBEAOLCHER'

(50) Latin Name: ***Dianthus* L.**
Varietal Denomination: Hilbeaolcher

(71) Applicant: Masahiko Sakuramoto, Minami-Alps (JP)

(72) Inventor: Masahiko Sakuramoto, Minami-Alps (JP)

( * ) Notice: Subject to any disclaimer, the term of this patent is extended or adjusted under 35 U.S.C. 154(b) by 0 days.

(21) Appl. No.: 14/999,998

(22) Filed: Jul. 25, 2016

(51) Int. Cl.
*A01H 5/02* (2006.01)

(52) U.S. Cl.
USPC ..... Plt./282

(58) Field of Classification Search
USPC ..... Plt./282
See application file for complete search history.

*Primary Examiner* — Annette Para
(74) *Attorney, Agent, or Firm* — C. A. Whealy

(57) ABSTRACT

A new and distinct cultivar of Carnation plant named 'Hilbeaolcher', characterized by its compact, uniformly mounding and upright to broadly spreading plant habit; relatively small leaves; freely flowering habit; red purple-colored single flowers; and good container and garden performance.

1 Drawing Sheet

Botanical designation: *Dianthus* L.
Cultivar denomination: 'HILBEAOLCHER'.

BACKGROUND OF THE INVENTION

The present invention relates to a new and distinct cultivar of Carnation plant, botanically known as *Dianthus* L., grown commercially as a container plant and hereinafter referred to by the name 'Hilbeaolcher'.

The new Carnation plant is a product of a planned breeding program conducted by the Inventor in Miniami-Alps City, Yamanashi, Japan. The objective of the breeding program is to create new container Carnation plants with numerous attractive single-type flowers.

The new Carnation plant originated from a cross-pollination made by the Inventor in Miniami-Alps City, Yamanashi, Japan in June, 2010 of a proprietary selection of *Dianthus* L. identified as code number JP 01, not patented, as the female, or seed, parent with a proprietary selection of *Dianthus* L. identified as code number JP 10, not patented, as the male, or pollen, parent. The new Carnation plant was discovered and selected by the Inventor as a single flowering plant from within the progeny of the stated cross-pollination in a controlled greenhouse environment in Miniami-Alps City, Yamanashi, Japan in September, 2011.

Asexual reproduction of the new Carnation plant by terminal cuttings propagated in a controlled greenhouse environment in Miniami-Alps City, Yamanashi, Japan since October, 2011 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbeaolcher'. These characteristics in combination distinguish 'Hilbeaolcher' as a new and distinct Carnation plant:

1. Compact, uniformly mounding and upright to broadly spreading plant habit.
2. Relatively small leaves.
3. Freely flowering habit.
4. Red purple-colored single flowers.
5. Good container and garden performance.

Plants of the new Carnation differ primarily from plants of the female parent selection in the following characteristics:

1. Plants of the new Carnation have smaller leaves than plants of the female parent selection.
2. Plants of the new Carnation have larger flowers than plants of the female parent selection.
3. Plants of the new Carnation and the female parent selection differ in flower color as plants of the female parent selection have light pink-colored flowers.

Plants of the new Carnation differ primarily from plants of the male parent selection in the following characteristics:

1. Flowers of plants of the new Carnation have fewer petals than flowers of plants of the male parent selection.
2. Plants of the new Carnation and the male parent selection differ in flower color as plants of the male parent selection have pink-colored flowers.

Plants of the new Carnation also can be compared to plants of *Dianthus* L. 'Sunflor Olivia', not patented. In side-by-side comparisons, plants of the new Carnation differ primarily from plants of 'Sunflor Olivia' in flower color as plants of 'Sunflor Olivia' have red and white-colored flowers.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant. The photograph comprises a side perspective view of a typical flowering plant of 'Hilbeaolcher' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 12° C. to 16° C., night temperatures averaged 12° C. and light levels averaged 7,000 lux. Plants used for the photograph and description were three months old. In the following description, color references are made to The Royal Horticultural Society Colour Chart, 2015 Edition, except where general terms of ordinary dictionary significance are used.

Botanical classification: *Dianthus* L. 'Hilbeaolcher'.

Parentage:

*Female, or seed, parent*.—Proprietary selection of *Dianthus* L. identified as code number JP 01, not patented.

*Male, or pollen, parent*.—Proprietary selection of *Dianthus* L. identified as code number JP 10, not patented.

Propagation:

*Type*.—By terminal cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; growth habit, moderate to low vigor.

*Plant height, soil level to top of foliar plane*.—About 13 cm.

*Plant height, soil level to top of floral plane*.—About 13.2 cm.

*Plant diameter or spread*.—About 20.8 cm.

*Lateral branches*.—Branching habit: Freely branching habit with about seven main (basal) stems; each main stem with about six lateral branches; pinching is not required. Length: About 10.3 cm. Diameter: About 1.75 mm. Internode length: About 3.8 cm. Strength: Strong. Aspect: Upright to outwardly spreading. Texture and luster: Smooth, glabrous; moderately glossy. Color, developing: Close to 145B. Color, developed: Close to 138A.

Leaf description:

*Arrangement*.—Opposite, simple; sessile.

*Length*.—About 4.7 cm.

*Width*.—About 8 mm.

*Shape*.—Narrowly oblanceolate; slightly curved.

*Apex*.—Acute.

*Base*.—Attenuate; decurrent.

*Margin*.—Finely dentate.

*Texture and luster, upper and lower surfaces*.—Smooth, glabrous; slightly glossy.

*Venation pattern*.—Anastomosing.

*Color*.—Developing leaves, upper surface: Close to between 143B and 144A. Developing leaves, lower surface: Close to 144A. Fully expanded leaves, upper surface: Close to NN137A; venation, close to NN137A. Fully expanded leaves, lower surface: Close to 138A; venation, close to 143A.

Flower description:

*Flower form and flowering habit*.—Single flowers arranged singly or in clusters of three; freely flowering habit numerous flowers developing during the flowering season; flowers face mostly upright to outwardly.

*Natural flowering season*.—Flowering is continuous from the spring to late summer in The Netherlands; plants begin flowering about eleven weeks after planting.

*Postproduction longevity*.—Flowers last about ten days on the plant; flowers not persistent.

*Fragrance*.—Moderately fragrant; sweet and pleasant.

*Flower buds*.—Length: About 2 cm. Diameter: About 5 mm. Shape: Elliptic to oblanceolate. Texture and luster: Smooth, glabrous; matte. Color: Close to 138B; towards the base, close to 145D; petal apices, close to 64A.

*Flower diameter*.—About 3 cm.

*Flower depth*.—About 2.5 cm.

*Petals*.—Quantity and arrangement: Five petals arranged in a single whorl. Length: About 2.8 cm. Width: About 1.8 cm. Shape: Spatulate. Apex: Praemorse. Base: Narrowly cuneate. Margin: Irregularly dentate. Texture and luster, upper surface: Mostly smooth and glabrous, proximally, sparsely pubescent; slightly velvety; matte. Texture and luster, lower surface: Smooth, glabrous; slightly velvety; matte. Color: When opening, upper surface: Close to 187B; towards the margins, apex and base, close to 61B and at the base, close to 145A to 145B. When opening, lower surface: Close to 59C to 59D; blotched with close to 195D and at the base, close to 145A to 145B. Fully opened, upper surface: Close to between 53A and 60A; towards the margins and apex, close to 67B; towards the base, close to N57A and at the base, close to 145A to 145B; venation, similar to lamina colors. With development, color becoming closer to darker than between 59A and 187B; towards the margins and apex, close to N66A to N66B; towards the base, close to N57B and at the base, close to 145B. Fully opened, lower surface: Close to 59C to 59D; blotched with close to 195D and at the base, close to 145A to 145B; venation, similar to lamina. With development, color becoming closer to 59C; blotched with close to 195D and at the base, close to 145B.

*Sepals*.—Quantity and arrangement: Five sepals arranged in a single whorl; proximal 30% portion of the sepals are fused into a campanulate-shaped calyx. Calyx length: About 1.6 cm. Calyx diameter: About 6 mm. Sepal length: About 1.6 cm. Sepal width, at base of "free" portion: About 3 mm. Shape: Narrowly oblong. Apex: Narrowly acute. Margin: Entire. Texture and luster, upper surface: Smooth, glabrous; glossy. Texture and luster, lower surface: Smooth, glabrous; matte. Color: When opening, upper surface: Close to 143C. When opening, lower surface: Close to 138B; towards the base, close to 145D. Fully opened, upper surface: Close to 143C; towards the apex, close to 182B. Fully opened, lower surface: Close to 143A; towards the base, close to 145A; towards the apex, close to 200B.

*Peduncles*.—Length: About 1.3 cm. Diameter: About 1.5 mm. Strength: Moderately strong. Aspect: About 22.5° from the stem axis. Texture and luster: Smooth, glabrous; glossy. Color: Close to 143A.

*Reproductive organs*.—Stamens: Quantity: About ten stamens per flower. Filament length: About 1.9 cm. Filament color: Close to NN155A; proximally, close to 145D; distally, close to N75A. Anther size: About 2 mm by 1 mm. Anther shape: Oblong. Anther color: Close to 156D. Pollen: Scarce. Pollen color: Close to 158D. Pistils: Quantity: About two per flower. Pistil length: About 1.4 cm. Stigma diameter: About 3 mm. Stigma shape: Pointed, spirally curved. Stigma color: Close to 77A. Style length: About 1 cm. Style color: Close to NN155A. Ovary color: Close to 144A to 144B. Fruits and seeds: Fruit and seed development have not been observed on plants of the new Carnation.

Disease & pest resistance: Plants of the new Carnation have not been observed to be resistant to pathogens and pests common to Carnation plants.

Garden performance: Plants of the new Carnation have been observed to have good garden performance and to tolerate high temperatures about 35° C. and to be suitable for USDA Hardiness Zones 5 to 9.

It is claimed:

1. A new and distinct Carnation plant named 'Hilbeaolcher' as illustrated and described.

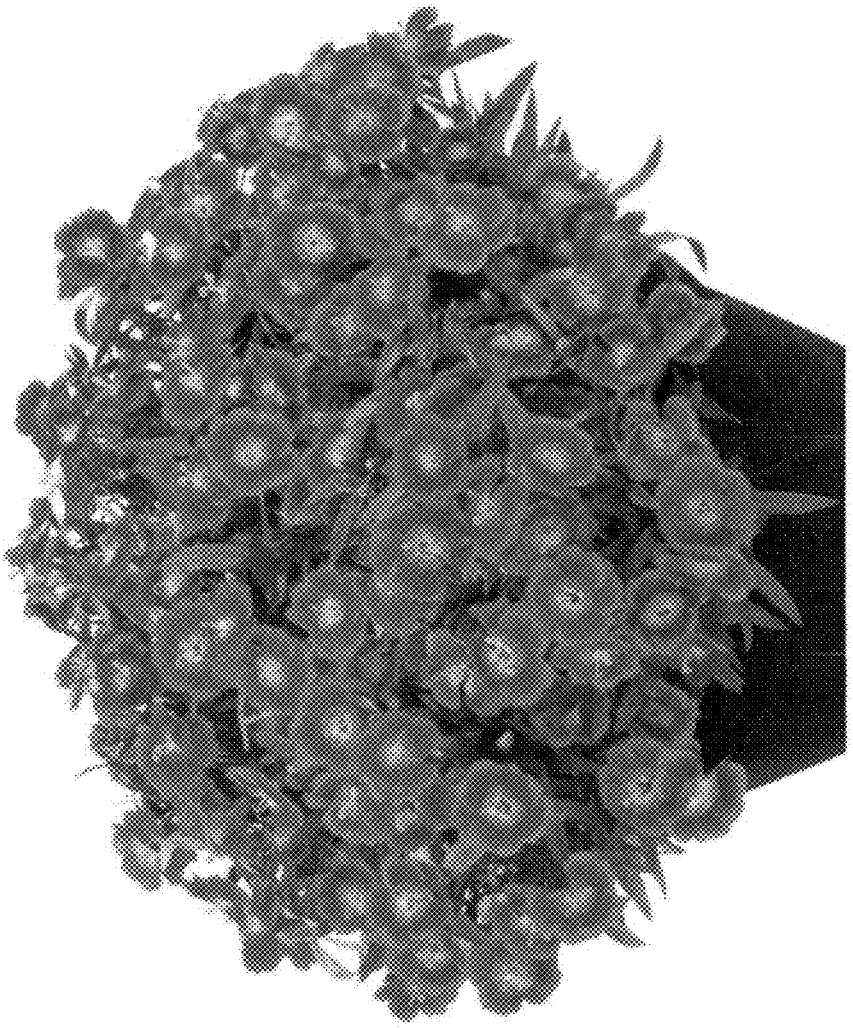

* * * * *